United States Patent [19]
Liu et al.

[11] Patent Number: 5,771,632
[45] Date of Patent: Jun. 30, 1998

[54] ARTIFICIAL SEED WITH A POWDER STRUCTURE FOR ANTI-CONTAMINATION

[76] Inventors: Sijiu Liu; Wannan Xu, both of 262 Harvard St. #8, Cambridge, Mass. 02139; Lily Qianli Liu, 2887 Hinman, Hanover, N.H. 03755; Qianye Liu, 36 Oxford St. #418, Cambridge, Mass. 02138

[21] Appl. No.: 717,711

[22] Filed: Sep. 23, 1996

[51] Int. Cl.$^6$ .............................. A01C 1/06; A01C 21/00; A01G 1/00; A01H 1/02
[52] U.S. Cl. ........................ 47/57.6; 47/DIG. 9; 800/200
[58] Field of Search ............................... 47/57.6, DIG. 9; 800/200

[56] References Cited

U.S. PATENT DOCUMENTS

| | | | |
|---|---|---|---|
| 5,250,082 | 10/1993 | Teng et al. ................................. | 47/57.6 |
| 5,382,269 | 1/1995 | Giroud-Abel et al. .................... | 47/57.6 |
| 5,427,593 | 6/1995 | Carlson et al. ........................... | 47/57.6 |
| 5,525,131 | 6/1996 | Asano ....................................... | 47/57.6 |

OTHER PUBLICATIONS

Dupis et al., Pharmaceutical Capsules as a Coating System for Artificial Seeds, Bio/Technology, vol. 12 Apr. 1994 pp. 385–389.

*Primary Examiner*—David T. Fox
*Assistant Examiner*—Kent L. Bell

[57] ABSTRACT

An artificial seed has a powder structure or powder padded layer as a sealing material for anti-contamination purpose. This powder layer, 2–30 mm preferably 5–20 mm in thickness, consists of numerous fine sandy hydrophobic particles. The openings among the particles are small and winding enough to block micro-organisms from penetrating this dry and nutrientless layer into the seed, but not enough to block the needed oxygen. The hydrophobic nature of the particles is also effective to block water permeation and microbes therein, but not effective to block the tissue to grow out of the seed. The powder layer can cover any exposed part of the artificial seed. For the artificial seeds with a water-proof tough shell, the powder layer covers only the mouth or mouths of the shell. But for those with a water-soluble capsule, or water-soluble film, it covers all over the contents of the seeds. In both cases, the powder layer is again covered with the water-soluble film to kept the powder particles in position. After sowing and watering the artificial seed in non-sterile soil, the water-soluble film is dissolved but the powder layer is still kept in position by the surrounding soil. The germination process is very much like that of a real botanical seed.

10 Claims, 2 Drawing Sheets

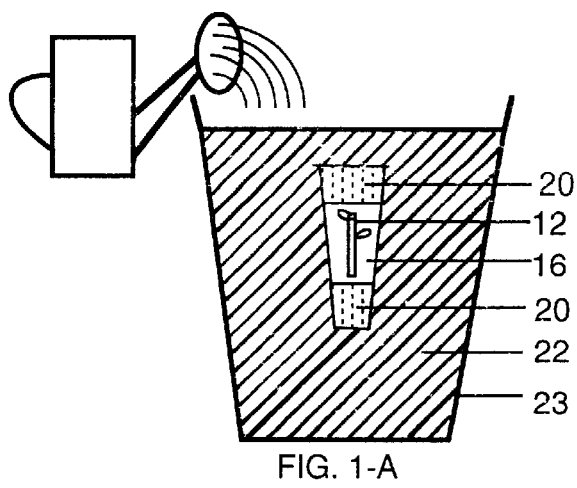
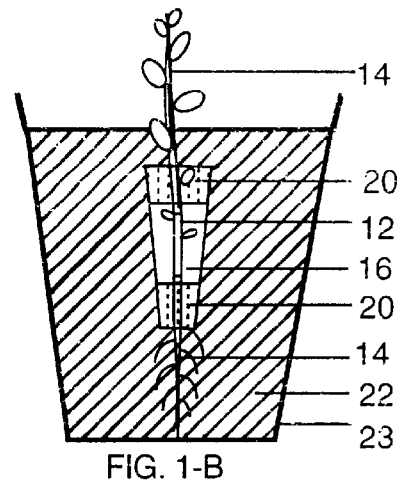
FIG. 1-A  FIG. 1-B
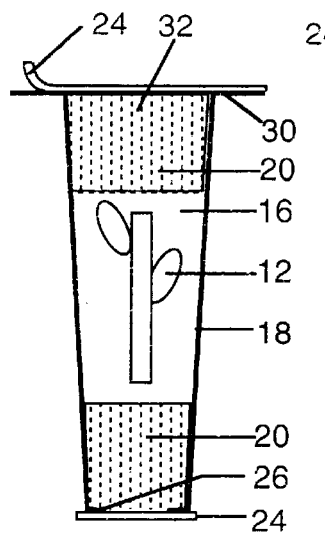
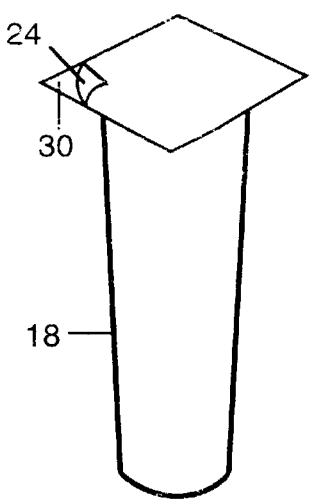
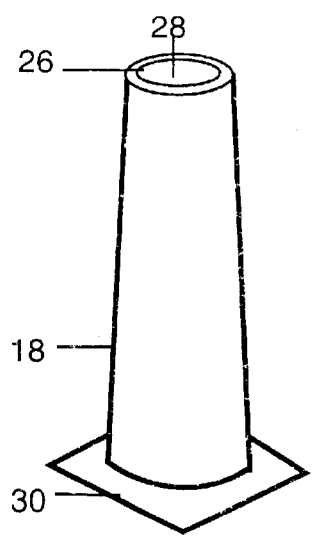
FIG. 2-A  FIG. 2-B  FIG. 2-C
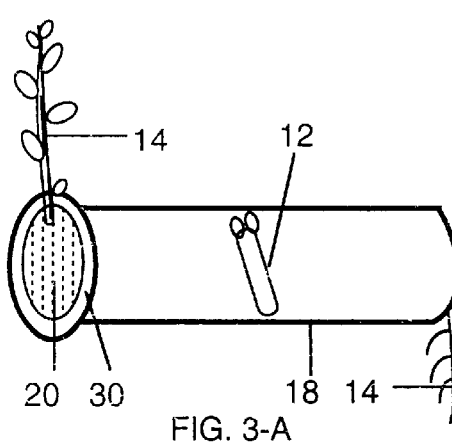
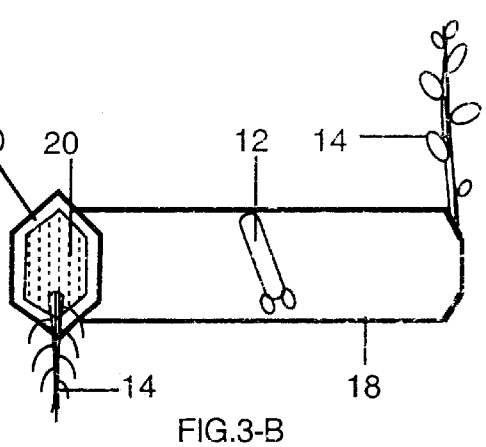
FIG. 3-A  FIG. 3-B

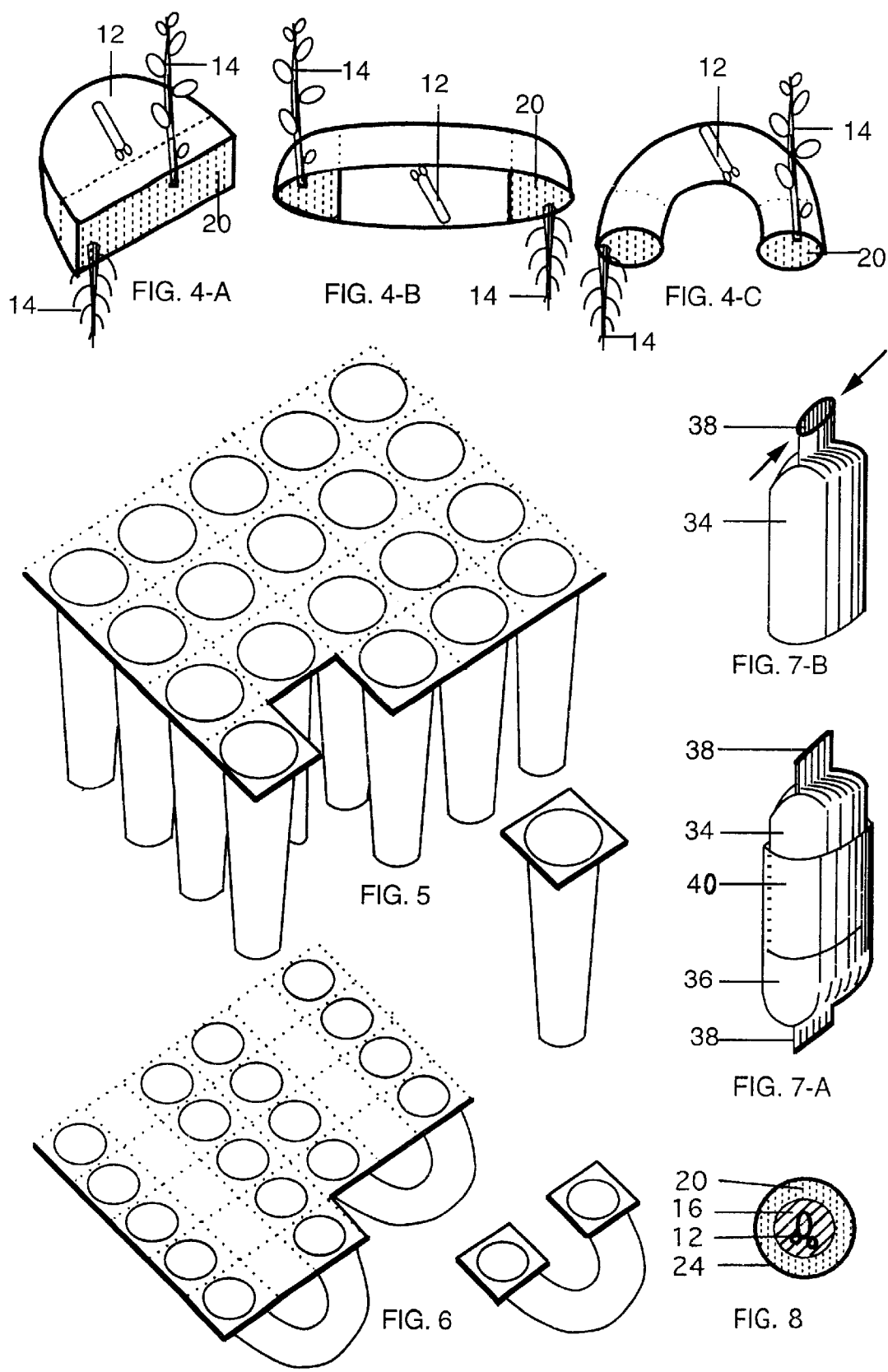

ARTIFICIAL SEED WITH A POWDER STRUCTURE FOR ANTI-CONTAMINATION

FIELD OF INVENTION

This invention relates to the analog of botanical seed, or artificial seed, particularly to a powder structure that prevents the artificial seed from contamination during germination.

BACKGROUND OF INVENTION

Artificial seeds, as the ultimate means of plant micro propagation, have the following advantages over conventional tissue culture plantlets or test-tube plants:

First, from the view point of the artificial seeds providers, the plant micro-propagation industry:

The artificial seeds exclude the need for greenhouse which is necessary for conventional test-tube plantlets in their hardening phase. The test-tube plantlets need a lot of culture space or growth room for their rooting and growing phases, while the artificial seeds exclude the need for most part of it. As a result, the providers can save money not only from the initial investment in building the greenhouse and growth room but also from the routine operation in the associated utilities. The providers can also save most of the associated skilled labors which count for the major component of the production cost. Furthermore, elimination of conventional rooting, growing, and hardening phases in manufacture procedures will shorten the time before delivery. All the above savings and advantages make it possible to greatly lower the prices and to exploit new potential markets in vegetable and woody plant industries.

Second, from the view point of the artificial seeds users, the farms and nursery owners:

The farmers and nursery owners can save a substantial amount of money in buying the artificial seeds than in buying the established test-tube plantlets. In the mean time, they don't have to invest in more growth room or greenhouse. Sowing the artificial seeds is much easier than otherwise to transplant the purchased plantlets which not all can survive the transplantation.

However, two problems have to be overcome before the current artificial seed technology can be used on a large scale. They are the problem of contamination in germination and the problem of insufficient gas exchange.

Artificial seeds in prior art were made naked by simply encapsulating the somatic embryos in hydrogels which are very susceptible to fungus or bacteria. This is especially true when sugar is contained in the capsule along with the somatic embryos.

In recent years, some artificial seeds are designed to be enclosed into a water-soluble dry shells which are coated on its inner surface with a water-proof film to protect the seeds from contamination and physical damage. Examples of this kind of artificial seeds can be seen in the U.S. Pat. No. 5,250,082 (Teng et al, Oct. 5, 1993), and U.S. Pat. No. 5,382,269 (Giroud-Abel et al, Jan. 17, 1995).

Although the dry shells and the water-proof films do protect the artificial seeds during storage and transportation, this protection is soon lost when the water-soluble shells are dissolved in the wet soil, and when the water-proof films are broken through by the growing tissues in the seeds. Because the water-proof film is very thin, only a fraction of a millimeter, the nutrients inside the seeds will easily permeate out and the microorganisms in the soil can easily invade into the seeds through the broken gaps. One month or so after the formation of the first broken gap, the artificial seeds still need to be protected for survival. Unfortunately, all the artificial seeds in prior art fail to provide such protection during this critical period.

Therefore, the artificial seeds in prior art have to be sowed on sterile agar medium, or sterile substrates, like sands or vermiculite. Their germination on the non-sterile soil greatly reduces the conversion frequency because of contamination of the artificial seeds.

In the U.S. Pat. No. 5,427,593 Carlson et al (Jan. 27, 1995) constructed a plastic outer shell with an opening thereof for their artificial seed. After inoculation of the somatic embryo, the opening is then sealed with a thin layer of wax. In this case, the protection of their artificial seeds, on the whole, is still dependent on the thin film (a layer of wax). As soon as the layer of wax is broken through by the growing tissue of the embryo, the protection is gone and the artificial seeds will inevitably be susceptible to contamination from the surrounding soil.

Another hurdle that halts the progress of artificial seeds technology is the gas exchange in hydrogel beads. Gas exchange was found to be poor in alginate gels, resulting in low conversion frequencies compared with non-encapsulated embryos (Redenbaugh et al 1988b, 1990a, 1991). Some efforts have been made toward this direction (as seen in the U.S. Pat. No. 5,236,469, U.S. Pat. No. 5,451,241 and many others). However, in prior art all the embryos are enclosed in a closed and sealed, volume-limited capsules or shells, which can only trap a limited amount of oxygen. This apparently is not enough to meet the great demand for oxygen during germination.

Because of the major problems of insufficient protection from contamination and insufficient gas exchange in prior artificial seeds technology, there has been no single company in the plant micro propagation industry that is able to commercialize the technology on a large scale.

OBJECTS AND ADVANTAGES OF INVENTION

Accordingly, it is an object of the present invention to provide a powder structure for anti-contamination which can effectively prevent the invasion of microorganisms during the critical germination period. Users then can sow the artificial seeds in non-sterile soil and get high conversion frequency.

It is another object of the invention to provide an unsealed enclosing means for the artificial seeds, so the embryo inside can get enough oxygen directly from the ambient during germination.

Still another object of our invention is to provide methods, steps and ideas for preparing the artificial seeds manually as well as in automation.

BRIEF DESCRIPTION OF THE DRAWINGS

FIGS. 1A–B longitudinal section view of a germinating artificial seed:

(A) before germination. (B) after germination.

FIGS. 2A–2C The details of the same artificial seed as in FIG. 1.

FIGS. 3A–3B Perspective views of the straight-tube type of artificial seeds which are in germination.

FIGS. 4A–4C Perspective views of the U-bottom type artificial seeds which are in germination.

FIG. 5 A part of shell cluster (one example for straight-tube type).

FIG. 6 A part of shell cluster (one example of U-bottom type).

FIGS. 7A–7B Composite type of artificial seeds with self-closing mouth.

FIG. 8 A transverse sectional view of a no-shell type of artificial seeds.

REFERENCE NUMERALS IN DRAWINGS

| | |
|---|---|
| 10 Artificial seed | 12 Meristematic tissue/embryo |
| 14 Plantlet | 16 Artificial endosperm/paste like medium |
| 18 Tough shell | 20 Hydrophobic powder layer |
| 22 Soil | 23 Pot |
| 24 Releasable film | 26 Inward mouth edge |
| 28 Lower mouth | 30 Outward mouth edge |
| 32 Upper mouth | 34 Receptacle part |
| 36 Lid part | 38 Self-closing mouth |
| 40 Overlap portion | |

SUMMARY OF INVENTION

An artificial seed comprising an isolated meristematic tissue which has potential to develop into a plantlet, an artificial endosperm which contains nutrients to nourish said tissue, an enclosing means which encloses, except at least one opening or mouth, the complex consisting of said tissue and said endosperm, and a piece of water-soluble film which covers said mouth and temporarily seals the artificial seed, wherein the improvement of the present invention is that a mass of hydrophobic powder which consists of numerous fine sandy hydrophobic particles, is deposited in a reserved space between said complex and said water-soluble film, so as to form a powder padded layer covering at least a part of the complex, whereby said powder padded layer blocks water permeation and microbes therein, while allows oxygen to get in and said tissue to grow out after said film being dissolved in wet soil.

One example of the above artificial seed is made of a section of plastic tube with two open ends or mouths; after inoculation of the artificial endosperm and the tissue, the two mouths are filled up with the above hydrophobic powder particles for anti-contamination; the two mouths are then covered with a piece of releasable film such as a water-soluble film to hold the powder in position. The releasable film will be weakened or dissolved away in the wet soil to allow the plantlet to grow out and oxygen to get in. This artificial seed can be sowed in the ordinary non-sterile soil like a real botanical seed.

DEFINITION AND DESCRIPTION OF THE MAJOR ELEMENTS

The following is the definitions and detailed description of the major components of the artificial seed from present invention:

HYDROPHOBIC POWDER

The conventional closures of plant tissue culture such as the film-like closure, the lid-like closure, etc. are designed not to be penetrated by the growing tissues inside containers, therefore, they can not be used as sealing material in artificial seeds. Unfortunately, artificial seeds in prior art have been adopting a coat, a water-proof film, a shell, or a capsule as the sealing material for their artificial seeds. They are in principle the same closure as in the plant tissue culture.

In the present invention, a mass of hydrophobic powder which consists of numerous fine sandy hydrophobic particles, is utilized as a sealing material for the artificial seed. The hydrophobic particles are deposited in the reserved space between the complex and the water-soluble film, so as to form a powder structure or powder padded layer beneath the water-soluble film. When the film is dissolved in wet soil, the hydrophobic, dry, and nutrientless powder layer, 2–30 mm preferably 5–20 mm in thickness, can effectively block micro-organisms from getting into the artificial seed, yet still allow oxygen to get in and the tissue to grow out because of the following characters of the particles:

(a) The hydrophobic powder layer consists of fine sandy particles preferably in round shape. The openings among the particles are small and especially winding enough to block the microorganisms, but not enough to block gas exchange.

(b) The powder particles are mobile or free flowing. They do not stick into aggregates. Any gap caused by the growing tissue from under the powder layer will be filled up instantly by the flowing particles, so that the penetration of the plant tissues does not cause contamination.

(c) Because of the powder particles' hydrophobic nature, the power is free of capillary water, so that no solution or water in the artificial endosperm can permeate out through the powder layer and no water or microorganisms therein from the soil can permeate into the artificial seed.

(d) The border gap in prior art (between the closure and the wall of container) is one of the major sources of contamination in plant tissue culture containers. However, there is no border gap between the powder layer and the enclosing means of the artificial seeds. The powder layer, essentially a powder closure, eliminates the border gap completely by its free flowing particles. The particles can fill any gaps which are equal or bigger than a single particle.

The fine sandy hydrophobic particles can be made by grinding any hydrophobic material (pure or mixture) whose resulting particles do not stick together and form aggregates. Eliminating extra fine particles with 200-mesh sieve can reduce the tendency of aggregation. Example of this kind is synthetic polymers such as some foamed plastics. The hydrophobic particles can also be made by grinding hydrophilic material and then coating it with hydrophobic material by a careful heating and stirring method known per se. An example of this kind is fine vermiculite particles coated with wax. Eliminating extra fine vermiculite particles before coating also gives better result. Different kinds of hydrophobic particles can be mixed and used in one powder layer. All the above hydrophobic particles can be sterilized by heating or radiation in paper bags before use.

ENCLOSING MEANS

Because of the delicacy of the complex, and the free flowing character of the hydrophobic powder, the artificial seed needs an enclosing means to enclose and hold them in position. The enclosing means should has enough strength, at least in dry state, to protect the artificial seed from handling damage before sowed into the soil. The enclosing means should also be releasable, at least at a part of the means, so as to provide one or more exits or mouths for the plantlet to grow out of the seed during germination.

The enclosing means can be a releasable film or coat, such as a water-soluble film. The water-soluble film can be made from natural polymers, such as starch. The water-softenable material such as the bathroom tissue is another example of the releasable film. The resistance to the penetrating force of the growing tissue will be lost or decrease when the film gets wet in the soil. After the film is dissolved or broken in the soil in which the artificial seed is sowed, the soil will keep the powder in position.

The enclosing means can also be a relatively hard shell or tough shell with enough strength in both dry and wet state, such as plastic, glass, or pottery. They can not be broken by the growing tissue during germination. In this case, enclosing means may have one or more open mouths as well as self-closing mouths or lids to allow the tissue to grow out.

According to the above description, both the releasable film and the tough shell can be used alone as an enclosing means. However, it is very ideal to make a enclosing means with a partial tough shell and a partial releasable film at different parts of the shell. Of course, in this case the self-closing ability is not needed. Unlike the sealed capsule or shell found in prior art, the tough shell in this case has one or more unsealed openings or mouths, covered with a piece of releasable film to temporarily close the seed. The mouths are re-openable during germination either by squeezing or by dissolving to provide a passage for the plant tissues to grow out through the hydrophobic powder layer and for gas exchange. Therefore, after the plantlets grow out of the mouth, the tough shells and the hydrophobic powder layer are still intact and protecting the artificial seeds until germination is completed.

The tough shell of our invention is made of either watertight material to prevent water loss for hydrated artificial seeds, or material which is water-permeable but macromolecule- and microorganism-impermeable, for dry artificial seeds. Both of the two kinds of materials are known per se in the field. The water-permeable shell can absorb water from soil during germination yet avoid contamination and loss of nutrients from the seed.

In either case, degradable materials are preferred in order to protect the environment. For hydrated artificial seed, degradable plastic, or paper impregnated with wax are recommended. For dry artificial seed, cellulose, the material used to make the dialytic tubes is suitable for making the tough shells.

The enclosing means constructed with one or more mouths can take a variety of shapes, either irregular or geometric. The geometric shapes comprise round to ellipse ball-like, tube-section-like, drum-like, pot-like, cubic-like, and barrel-like with different transverse sections. The irregular shapes include the sections of curved tubes, the irregular barrels, the modified boxes, the tapered tubes, and the U-bottomed pots. The most favorable shapes are sections of tube with two mouths at the ends. The tube shells may be tapered cylindrical (FIG. 1 and FIG. 2), straight cylindrical (FIG. 3), or U-shaped (FIG. 4), etc. The tough shells may also be constructed with only one mouth, as shown in FIG. 4.

The tough shells can be made in easily separable clusters, each consisting of dozens or hundreds of tough shells (FIG. 5 and FIG. 6) in order to increase the efficiency of manual operation, and auto- or semi-automation.

MERISTEMATIC TISSUE

The meaning of the meristematic tissue here is an isolated unit of plant germplasm body other than the botanical seed, especially those germplasms whose botanical seeds do not breed true and must be propagated vegetatively, such as some ornamentals, fruit and forest elite trees; and those whose botanical seeds need special hybridization manipulations and extra cost to reproduce, such as hybrid food crops and some hybrid vegetables. The isolated unit that represents the meristematic tissue includes but not limited to somatic embryos, the explants of axillary branches, nodal sections, adventitious shoots, buds, and the explants of protocorm, bulblet, and tubercle.

Somatic embryos are the best meristematic tissues for large scale artificial seed industry. Explants that are currently used in plant micro propagation industry, such as the nodal sections, axillary branches, adventitious shoots, etc. are the best meristematic tissues for manually made artificial seeds to substitute current products of the established tissue cultured plantlets or test-tube plantlets. Making the artificial seeds manually is much more efficient than in vitro culturing the test-tube plantlets by the existing routine process of rooting, hardening, and transporting.

ARTIFICIAL ENDOSPERM

The term artificial endosperm means a semisolid or paste-like medium that suspends, carries, and nourishes the meristematic tissues or embryos.

Unlike the known drop-encapsulation method, the nutrients, the non-toxic hydrophilic carrier or support, and water are first mixed into a semisolid or paste-like medium. Then the meristematic tissues are mixed into the paste-like medium to form a mixture or complex. Finally, the complex is squeezed through a nozzle into the enclosing means. The squeezing is similar to the squeezing tooth paste. The mixing of the complex should be at a proper ratio, so as to ensure that one enclosing means has at least one embryo.

In the auto- or semi-automation operations, multiple nozzles can be used to squeeze dozens or even hundreds of embryos each time, thus can achieve a much higher efficiency than the drop-encapsulation method. In the manual operation, the artificial endosperm can be squeezed into the enclosing means first, before the tissues or embryos are inoculated.

The support can be hydrophilic polymer or hydrophilic mineral particles. To hold the nutrients solution, to suspend, to carry, and to protect the embryos or meristematic tissues are the major functions of the support. The selection of the support depends on the type of artificial seeds. For hydrated artificial seeds, the natural polymer such as agar is recommended. It provides a semisolid and smooth texture to reduce possible damage to the embryos when the complex is squeezed into the enclosing means. For the dry artificial seeds, hydrophilic mineral such as the fine vermiculite particles is recommended, because the particles will retain their texture after dehydration and rehydration circle.

DETAILED DESCRIPTION OF INVENTION

STRAIGHT-TUBE TYPE

As shown in FIG. 1, FIG. 2, and FIG. 3, in spite of the slight difference in transverse sections of this type, the tough shells of the artificial seeds are all sections of straight tubes. The tapered tube shell shown in FIG. 1 and FIG. 2 is one of the most preferred embodiments in this invention.

FIG. 1 shows the germination process of the artificial seed in the present invention. The artificial seed 10 comprises at least one meristematic tissue or embryo 12, which will finally developed into a plantlet 14; a portion of paste-like, semisolid medium or artificial endosperm 16; a tapered straight-tube type tough shell 18, in which the embryo and the endosperm are inoculated in the center, and the space inside the two ends is reserved; a mass of hydrophobic powder 20 consisting of numerous fine sandy hydrophobic particles and filling up the space; and finally a piece of releasable films 24 covering the shell and keeping the powder in position. The artificial seed 10 is sowed in non-sterile soil 22 in a pot 23. FIG. 1-A shows the artificial seed sowed before germination, and FIG. 1-B after germination with the shoot and root growing out of the powder layers into the soil 22 like a real seed.

For detailed structures of FIG. 1, FIG. 2-A illustrates a longitudinal section view; FIG. 2-B, a corresponding perspective view; and FIG. 2-C, a view of an empty shell. Shown in FIG. 2-A there is a piece of releasable film or coat 24 stuck or covered on the inward mouth edge 26 of the lower mouth 30, and another piece on the outward mouth edge 28 of the upper mouth 32 (FIG. 2-B and FIG. 2-C). The releasable film 24 is to enclose and hold the powder layer 20 in position before sowing.

Thus the whole assembly looks like a small closed test tube, but can be handled and sowed in the non-sterile soil 22 in farm or nursery. Finally, it can germinate into a plantlet like a normal botanical seed free from contamination. The plantlet hardens itself gradually when slowly emerging from the powder layer and soil. This emerging and hardening process is exactly the same as that of botanical seedlings in nature (see FIG. 1, FIG. 3 and FIG. 4).

FIG. 3 shows the germination process of other artificial seeds of this type with a cylindrical tube (A), or a hexagonal tube (B). If production of the artificial seed is in automation, the embryos are randomly oriented in the shells. It is preferable to sow the seeds horizontally in the soil to ease the embryo growing out, just like the natural seeds sowed in the soil as illustrated in FIG. 3 and FIG. 4.

The method for preparing the straight tube type of artificial seeds includes the following steps:

(a) manufacturing and sterilizing the straight tube shells 18;

(b) preparing the paste-like medium 16 with hydrophilic polymer, such as agar, for hydrated artificial seeds, or hydrophilic mineral particles, such as vermiculite for dry artificial seeds;

(c) preparing the complex by mixing the meristematic tissues or embryos 12 with the paste-like medium 16 at a proper ratio;

(d) covering the lower mouth edge 26 from outside or inside of the shell to temporarily close the lower mouth 30 with a sheet of releasable film 24;

(e) filling the lower mouth with hydrophobic powder 20 up to about ¼ of the volume of the shell 18;

(f) squeezing the above complex into the shell to about ½ volume of the shell, reserving the rest ¼ space in the upper mouth;

(g) filling in the hydrophobic powder 20 again into the space reserved;

(h) covering the upper mouth 32 with a sheet of releasable film 24 on the outward edge 28 to temporarily seal the whole shell;

(i) storing the artificial seed in refrigerator in sealed plastic bag for hydrated seeds, or dehydrating the seeds and storing them in room temperature for dry artificial seeds.

U-BOTTOM TYPE

The tough shells of U-bottom type are characterized with a U-shaped bottom for guiding the roots or shoots which if oriented towards the bottom, will be able to make a U-turn and grow out of the mouth.

FIG. 4 illustrates the horizontally sowed artificial seeds of this type and normal plantlets germinated without much twisting. FIG. 4-A is an example of U-bottomed shells with only one mouth, while FIG. 4-B and FIG. 4-C are examples of U-bottomed shells with two mouths. In comparison, the U-bottom shell has two advantages over the straight-tube shell: First, one common sheet of the releasable film 24 can cover both mouths at the same time. Second, the two mouths can be filled up with the hydrophobic powder at the same time. On the other hand, the advantage of the tapered cylindrical shells is that the empty shells can be piled up together for packaging.

The method for preparing the U-bottom type of the artificial seeds includes the following steps:

(a) manufacturing and sterilizing the tough shells 18;

(b) preparing the paste-like medium 16 with polymer such as agar for hydrated artificial seeds, or hydrophilic mineral such as vermiculite for dry artificial seeds;

(c) preparing the complex by mixing the paste-like medium and the embryos 12 at a proper ratio;

(d) squeezing the above complex into the U-bottom shells 18 up to about ½ volume in the central part of the shell, reserving the rest space in the two mouths;

(e) filling the reserved space in the shell from the two mouths 30 & 32 with the hydrophobic powder 20;

(f) covering both mouths with a sheet of releasable film 24 on the mouth edge to temporarily close the whole shell;

(g) storing the artificial seeds in refrigerator in sealed plastic bags for hydrated artificial seeds, or dehydrating them for dry artificial seeds.

COMPOSITE TYPE

In this type the tough shell of the artificial seed is composed of a receptacle part 34 and a lid part 36 (FIG. 7-A). The two parts are fitting with each other and are overlapping a substantial portion 40. The composite type of artificial seed can be made with at least one open mouth or with self-closing mouth.

FIG. 7-B shows the self-closing mouth 38 which can temporarily close the mouth and can be used with any version of the present invention. The self-closing mouth is normally closed by resilient force on the opposite edges of the mouth, but can be squeezed open by the growing tissue or by a foreign force against the resilient force as shown by the arrows in FIG. 7-B.

The self-closing mouth can have a variety of other forms such as self-closing lid on the mouth or on any other position of the enclosing means to temporarily close the mouth.

The self-closing mouth and the self-closing lid are used for keeping the hydrophobic powder in position without the need of the releasable film. Therefore, the releasable film is not absolutely necessary for the present artificial seeds. The method for preparing the composite type artificial seeds includes the following steps:

(a) manufacturing and sterilizing the tough shells that have the self-closing mouth or lid;

(b) preparing the semi-solid or paste-like medium with hydrophilic support (polymer for hydrated artificial seeds, or hydrophilic mineral for dry artificial seeds);

(c) preparing the complex by mixing the embryos with the paste-like medium, at a proper ratio;

(d) filling about ⅓–½ of the volume of both the receptacle part and the lid part with the hydrophobic powder layer;

(e) squeezing the above complex into the rest of the space in the receptacle part only;

(f) turning over the receptacle part and inserting into the lid part until a substantial portion of the two parts are overlapped;

(g) storing the hydrated artificial seeds in refrigerator, or dehydrating the dry artificial seeds and storing them at room temperature.

NO-SHELL TYPE

The no-shell type of artificial seed has the complex consisting of the tissue and the endosperm to be completely surrounded by hydrophobic powder layer to protect the artificial seed against contamination, and an enclosing means which is a releasable film such as a water-soluble film that fully encloses the hydrophobic powder layer to provide a dry strength against the handling damage.

The advantage of the no-shell type is its simplicity in structure (see FIG. 8) which may be very valuable in automation, wherein the squeezing of the complex and the covering of the hydrophobic powder layer can be combined into one step.

MANUAL-ARTIFICIAL SEEDS

Any of the above described type of our artificial seeds, if prepared manually, can also be called manual-artificial seeds. A manual method for preparing the artificial seeds is that: instead of preparing a complex or mixture as described above, the paste-like medium 16 is added first, then the embryo 12 is inoculated into the enclosing means manually.

Since these manual steps are already a part of the routine operation of conventional plant tissue culture, the artificial seeds in the present invention is now ready to be carried out in any plant micro propagation company before the automation machinery is available. Artificial seeds in prior art, however, were not part of the routine operation of conventional plant tissue culture and can not be carried out immediately without additions of new machinery.

The present invention also abolishes the notion that the artificial seeds must be made as small as possible, so that they look like real botanical seeds. In fact, a single botanical seed in nature can be as big as a walnut or chestnut seed. Other examples of big seeds are mango and coconut seeds (also a fruit) which are hundreds or even thousands times bigger than the rice or wheat seeds. Therefore, the most important characteristics of a seed is not its size or weight, but rather its ability to give rise to a whole plantlet under non-sterile germination condition. Making bigger artificial seeds is a practical step to bridge the artificial seed and plant tissue culture technologies.

The same is true about the appearance of the artificial seeds. Not all seeds in nature are of round or elliptical shape. Some of them are as short as a disc, others are as long as a stick. In our invention the artificial seeds can be made into a variety of sizes and shapes.

We believe that bigger artificial seeds can promote and benefit the plant micro propagation industry immediately. The size range of the manual-artificial seeds could be 10–100 mm, preferably 30–60 mm in length, and proportional in width. Of course this does not exclude smaller artificial seeds. Improvements made in automation equipment and large scale culture of somatic embryo using bioreactor technology will also no doubt benefit the artificial seed technology.

We claim:

1. An artificial seed comprising an isolated meristematic tissue which has potential to develop into a plantlet, an artificial endosperm which contains nutrients to nourish said tissue, an enclosing means which encloses, except at least one opening or mouth, a complex consisting of said tissue and said endosperm, and a piece of water-soluble film which covers said mouth and temporarily seals the artificial seed, wherein a mass of hydrophobic powder which consists of numerous fine sandy hydrophobic particles, is deposited in a reserved space between said complex and said water-soluble film, so as to form a powder padded layer covering at least a part of the complex, whereby said powder padded layer blocks water permeation and microbes therein, while allows oxygen to get in and tissue to grow out after said film being dissolved in wet soil, wherein said hydrophobic powder is made from hydrophilic particles which are coated with hydrophobic material.

2. The artificial seed of claim 1, wherein said powder padded layer is 2–30 mm in thickness.

3. The artificial seed of claim 1, wherein said hydrophobic powder is made from hydrophobic material or materials.

4. The artificial seed of claim 1, wherein said enclosing means has at least one self-closing mouth whose opposite edges have resilient force towards each other, so as to releasably close said mouth normally.

5. The artificial seed of claim 1 wherein said enclosing means is a section of tapered tube.

6. The artificial seed of claim 1, wherein said enclosing means is a U-shaped tube with two mouths facing to the same direction.

7. The artificial seed of claim 1, wherein said enclosing means has only one open mouth and one domed-like bottom.

8. The artificial seed of claim 1, wherein said meristematic tissue comprises an isolated unit of plant germplasm body other than botanical seeds, said plant germplasm comprising those whose botanical seeds do not breed true and must be propagated vegetatively, or those whose botanical seeds need hybridization manipulations and extra cost to produce.

9. An automated procedure for preparing the artificial seed of claim 1 comprising the steps of:

(a) Manufacturing and sterilizing said enclosing means;

(b) Preparing said complex by mixing said meristematic tissues into said artificial endosperm at a proper ratio, so that each enclosing means can contain at least one meristematic tissue;

(c) Squeezing a portion of the above complex into each enclosing means reserving a space with predetermined volume inside each mouth;

(d) Filling the reserved space up to the mouth edge with said hydrophobic powder;

(e) Covering all mouths with a piece of water-soluble film; omitting this step when using the enclosing means with said self-closing mouth;

(f) Storing hydrated artificial seeds by refrigeration or dry artificial seeds by dehydration.

10. A manual method for preparing the artificial seed of claim 1 comprising the following steps:

(a) Manufacturing and sterilizing said enclosing means;

(b) Preparing said artificial endosperm and adding a portion of it into each enclosing means, reserving a space with predetermined volume inside each mouth;

(d) Inoculating said tissues into said enclosing means;

(e) Filling the reserved space up to the mouth edge with said hydrophobic powder;

(f) Covering all the mouths with a piece of water-soluble film, omitting this step when using the enclosing means with said self-closing mouth;

(g) Storing hydrated artificial seeds by refrigeration, or artificial seeds by dehydration.

* * * * *